United States Patent
Tiedtke

(10) Patent No.: US 8,918,188 B2
(45) Date of Patent: Dec. 23, 2014

(54) ELECTRODE ARRAY AND METHOD OF MANUFACTURING SAME

(75) Inventor: Hans-Jürgen Tiedtke, Bonn (DE)

(73) Assignee: Pixium Vision SA, Paris (FR)

( * ) Notice: Subject to any disclaimer, the term of this patent is extended or adjusted under 35 U.S.C. 154(b) by 273 days.

(21) Appl. No.: 13/120,749

(22) PCT Filed: Sep. 26, 2008

(86) PCT No.: PCT/EP2008/008225
§ 371 (c)(1),
(2), (4) Date: May 18, 2011

(87) PCT Pub. No.: WO2010/034331
PCT Pub. Date: Apr. 1, 2010

(65) Prior Publication Data
US 2011/0257716 A1   Oct. 20, 2011

(51) Int. Cl.
*A61N 1/18* (2006.01)
*A61N 1/05* (2006.01)

(52) U.S. Cl.
CPC ............. *A61N 1/0543* (2013.01); *A61N 1/05* (2013.01)
USPC ................ 607/116; 607/53; 607/54

(58) Field of Classification Search
CPC . A61N 1/0543; A61N 1/36046; A61B 5/6821
USPC ............. 607/53, 54, 115, 116, 141; 600/383
See application file for complete search history.

(56) References Cited

U.S. PATENT DOCUMENTS

| | | | | |
|---|---|---|---|---|
| 4,758,222 A | * | 7/1988 | McCoy | 604/95.05 |
| 5,105,811 A | * | 4/1992 | Kuzma | 607/57 |
| 5,166,292 A | | 11/1992 | Pottiger et al. | |
| 5,279,559 A | * | 1/1994 | Barr | 604/95.05 |
| 5,632,841 A | * | 5/1997 | Hellbaum et al. | 156/245 |
| 5,824,031 A | * | 10/1998 | Cookston et al. | 607/122 |

(Continued)

FOREIGN PATENT DOCUMENTS

| | | |
|---|---|---|
| DE | 102006008050 | 8/2007 |
| WO | WO 2008/103195 | 8/2008 |

OTHER PUBLICATIONS

International Search Report and Written Opinion for International Application No. PCT/EP2008/008225 dated Feb. 19, 2009.

*Primary Examiner* — Carl H Layno
*Assistant Examiner* — Eugene Wu
(74) *Attorney, Agent, or Firm* — Workman Nydegger

(57) ABSTRACT

The present invention provides an electrode array for a medical implant device, comprising a substrate supporting a plurality of electrodes, the substrate comprising at least two layers of material including a first layer and a second layer, wherein the first layer of material and the second layer of material have different coefficients of thermal expansion. The plurality of electrodes may be supported on the first layer of material, and are preferably incorporated in and/or project from the second layer of material. The second layer of material may itself have a layered structure comprising multiple material layers, with the plurality of electrodes incorporated within the said multiple material layers. The first layer of material preferably has a higher coefficient of thermal expansion than the second layer of material. The invention furthermore provides a medical implant device including an electrode array according to the invention, and a method of manufacturing such an electrode array.

19 Claims, 1 Drawing Sheet

(56) References Cited

U.S. PATENT DOCUMENTS

| | | | |
|---|---|---|---|
| 5,977,689 A * | 11/1999 | Neukermans | 310/324 |
| 6,245,444 B1 * | 6/2001 | Marcus et al. | 428/616 |
| 6,970,746 B2 * | 11/2005 | Eckmiller et al. | 607/116 |
| 7,127,301 B1 | 10/2006 | Okandan et al. | |
| 7,604,353 B2 * | 10/2009 | Koga et al. | 351/221 |
| 8,275,432 B2 * | 9/2012 | Kuhn et al. | 600/310 |
| 2003/0093139 A1 * | 5/2003 | Gibson et al. | 607/137 |
| 2003/0195601 A1 * | 10/2003 | Hung et al. | 607/116 |
| 2007/0265665 A1 * | 11/2007 | Greenberg et al. | 607/2 |

\* cited by examiner

ELECTRODE ARRAY AND METHOD OF MANUFACTURING SAME

CROSS-REFERENCE TO RELATED APPLICATIONS

This application is a U.S. Nationalization of PCT International Application No. PCT/EP/2008/008225 filed Sep. 26, 2008, entitled "ELECTRODE ARRAY AND METHOD OF MANUFACTURING SAME," which is incorporated herein by reference in its entirety

TECHNICAL FIELD

The present invention relates to an electrode array and to a method of manufacturing an electrode array. More particularly, the invention relates to a stimulation electrode array for stimulating nerve cells in a human or animal body and a method of manufacturing same. The electrode array of the present invention is particularly designed for use in a medical implant device and, more particularly, in a retinal implant.

BACKGROUND OF THE INVENTION

Electrodes for use in medical implant devices are advantageously designed to be in close contact with the tissue they are intended to stimulate. Where the tissue to be stimulated has a non-planar (e.g. curved) surface profile, problems can arise in ensuring and maintaining the desired contact between the electrodes and the tissue to be stimulated over an entire area of the electrodes of the implant device. In cases where an electrode array includes only a few electrodes distributed over a very small area, the surface profile of the tissue to be stimulated will usually have little impact on the desired electrical contact. As the number of the electrodes and, therefore, the size of the electrode array increases, however, a curvature in the surface profile of the tissue becomes increasingly significant. The curved surface of the retina is one example of an area of the body which presents particular difficulties in achieving the desired contact between the electrodes of a retinal implant and the surface of the tissue containing the nerve cells to be stimulated.

The application of pressure to an implant device and/or to the electrodes of the implant device in order to achieve and/or maintain intimate contact between the electrodes and the tissue to be stimulated is generally undesirable as this can readily lead to irritation and even inflammation of the tissue. One solution to this problem is to design an electrode array which is highly flexible so that it is able to readily adapt itself to the profile of the underlying tissue surface. Such a high degree of flexibility, however, generally requires a very low material thickness and renders handling of the electrode array and/or of the implant device particularly difficult. A very high degree of flexibility in the electrode array also has the additional disadvantage that the electrodes and the current paths incorporated therein can become more susceptible to damage during handling and/or during implantation.

An alternative proposal involves moulding an electrode array of the implant device to have a predefined curvature corresponding to the surface profile of the tissue to be stimulated. This proposal, however, also has the disadvantage that the manufacture of such an electrode array would be problematic. In particular, either a finished substrate that already supports the electrodes of the electrode array would have to be shaped in a mould, thereby introducing an additional production step and providing further opportunities for the electrodes and current paths of the array to sustain damage, or alternatively, the substrate would have to be moulded before the application of the electrodes. This latter option, however, is not possible using the current production techniques, in which the electrodes are manufactured on a flat wafer.

Consequently, there exists a need for a new and improved electrode array for a medical implant device, and a method of producing same. In particular, it would be desirable to provide an electrode array for a medical implant device which is able to be specifically configured or tailored to suit a particular surface profile of the tissue to be stimulated.

SUMMARY OF THE INVENTION

The present invention provides an electrode array as defined in claim 1, and a method of manufacturing an electrode array as defined in claim 15. The present invention also provides a medical implant device incorporating such an electrode array. Preferred features of the invention are recited in the dependent claims.

Thus, the present invention provides a stimulation electrode array for a medical implant device, comprising a substrate which supports a plurality of electrodes. The substrate comprises at least two layers of material including a first layer and a second layer, wherein the first layer of material and the second layer of material have different coefficients of thermal expansion. The first and second layers in the substrate are, of course, desirably electrically insulating, and preferably consist of polymer material. Thus, the substrate of the electrode array preferably comprises a layered polymer film.

In a preferred embodiment of the invention, the first layer of material supports the plurality of electrodes. Furthermore, the plurality of electrodes preferably extend to and/or project from an outer surface of the substrate in such a manner that the electrodes are adapted for electrical contact with tissue in a human or animal body.

In a preferred embodiment of the invention, the first layer of material has a higher coefficient of thermal expansion than the second layer of material. The first layer of material preferably forms an outer layer of the substrate. Furthermore, the second layer of material may also form an outer layer of the substrate.

In a preferred embodiment of the invention, an outer surface of the substrate, at which the plurality of electrodes are adapted for electrical contact with the tissue in a human or animal body, is curved and, preferably, convexly curved. In other words, the plurality of electrodes preferably extend to and/or project from a convexly curved outer surface of the substrate. The substrate is able to present such a curved outer surface as a result of the fact that the first and second layers of the substrate have different coefficients of thermal expansion.

During production of the electrode array, the first and second layers of the substrate are preferably bonded, fused, cured or otherwise combined with one another in a flat condition at a temperature that is either elevated or reduced compared to a normal operating temperature for the electrode array. Accordingly, a temperature differential exists (i.e. a change in temperature occurs) between that production phase and the normal operation of the electrode array. This temperature change induces stresses or forces between the first and second layers of the substrate which act to deform or re-shape the substrate, and thereby endow the electrode array with a desired form. In particular, if the temperature change between production and normal service or operation of the electrode array is a significant temperature increase, the substrate layer having the higher coefficient of thermal expansion will tend to form a convexly curved outer surface. On the other hand, if the temperature change between production and normal operation of the electrode array is a significant temperature decrease or reduction, the substrate layer having the higher coefficient of thermal expansion will tend to form a concavely curved outer surface.

Because the materials of the first and second layers of the substrate are typically polymer materials which are bonded, fused and/or cured to form a layered structure at relatively high temperatures (e.g. in the range of 200° C. to 400° C.) compared to room temperature (e.g. 22° C.) or body temperature for a human or animal (e.g. 37° C.) at which the electrode array will typically operate, the temperature change between production and the operation of the electrode array in a medical implant device will be a significant temperature reduction. In such a case, the substrate layer having the higher coefficient of thermal expansion will tend to form a concavely curved outer surface. Thus, where the electrode array is intended to be employed in a retinal implant device, in which the plurality of electrodes are to be incorporated in and/or project from a second layer of the substrate having a convexly curved outer surface complementing a concave surface profile of the retina, the first layer of polymer material in the substrate will preferably have a higher coefficient of thermal expansion than the second layer.

The degree of curvature which is generated in the electrode array as a result of the different coefficients of thermal expansion of the first and second layers will depend, for example, upon the respective magnitude of the coefficient of thermal expansion (also called "CTE") of each of the first and second layers, as well as the thickness of each of these layers. The elasticity of the particular material(s) forming the layers will naturally also influence the degree of curvature generated.

In a preferred embodiment of the invention, the material(s) employed in the substrate is/are polymer material(s), and more particularly, bio-compatible polymer material(s). In this connection, the polymer material(s) is/are preferably selected from the group consisting of polyimide, parlyene, and silicone. It will be appreciated that a polymer material selected for the substrate layers may be coated to ensure its bio-compatibility. For example, a parlyene coating may be applied to the material at an outer surface of the substrate.

In a preferred embodiment of the invention, the CTE of the first layer is in the range of about 20 ppm/° C. (i.e. $20\times10^{-6}/$° C.) to about 40 ppm/° C. (i.e. $40\times10^{-6}/$° C.).

In a preferred embodiment of the invention, the CTE of the second layer is in the range of about 1 ppm/° C. (i.e. $1\times10^{-6}/$° C.) to 10 ppm/° C. (i.e. $10\times10^{-6}/$° C.), and more preferably in the range of about 1 ppm/° C. (i.e. $1\times10^{-6}/$° C.) to 5 ppm/° C. (i.e. $5\times10^{-6}/$° C.).

In a preferred embodiment of the invention, the first layer is a substantially uniform layer which extends with substantially uniform thickness over a surface of the substrate. In an alternative embodiment, however, the first layer may comprise a plurality of discrete or separate regions having a coefficient of thermal expansion different from the coefficient of thermal expansion of the second layer.

In a preferred embodiment of the invention, the second layer is a substantially uniform layer which extends with substantially uniform thickness over the substrate. Preferably, the second layer itself has a layered structure and comprises multiple material sub-layers. Thus, in a preferred embodiment, the second layer incorporates the plurality of electrodes within the said multiple material sub-layers. That is, the electrodes may be positioned or seated on one of the sub-layers and may extend to and/or project from an outer surface of the second layer.

In a preferred embodiment of the invention, the thickness of each layer and/or each sub-layer of the substrate is in the range of 0.1 µm to 100 µm, and more preferably in the range of 1 µm to 50 µm. In a particularly preferred embodiment, the thickness of each layer and/or each sub-layer of the substrate is in the range of 1 µm to 10 µm. For example, each layer and/or each sub-layer of the substrate may have a thickness of about 4 to 5 µm.

According to another aspect, the present invention provides a medical implant device for stimulating nerve cells in a human or animal body, the implant comprising an electrode array of the invention as described above. Preferably, the medical implant device is a retinal implant for stimulating nerve cells of the retina.

According to a further aspect, the present invention provides a method of manufacturing an electrode array, comprising the steps of:
  applying a first layer of material having a first coefficient of thermal expansion on a base or support structure;
  applying a second layer of material having a second coefficient of thermal expansion different from the first coefficient of thermal expansion on the first layer;
  combining the first layer and the second layer to form a substrate of the electrode array at a temperature different to a normal service temperature or operation temperature of the electrode array.

In a preferred embodiment of the invention, the step of combining the first layer and the second layer takes place at a significantly elevated temperature relative to a normal service temperature or operation temperature of the electrode array.

In a preferred embodiment of the invention, the step of combining the first layer and the second layer to form the substrate of the electrode array includes bonding, fusing, and/or curing the first layer and the second layer.

In a preferred embodiment of the invention, the step of combining the first layer and the second layer takes place on a substantially flat supporting structure, such that the substrate is substantially flat at the combining temperature. In this regard, the base or support structure preferably presents a substantially flat or planar surface, upon which the step of combining the first layer and the second layer takes place.

In a preferred embodiment of the invention, the method further comprises the step of combining a plurality of electrodes with the substrate such that the plurality of electrodes extend to and/or project from an outer surface of the substrate for electrical contact with tissue in a human or animal body. The step of combining the plurality of electrodes with the substrate includes applying the plurality of electrodes to the substrate, and more particularly applying the plurality of electrodes, preferably together with connecting conductor tracks, circuitry or wiring, to the first layer and/or to the second layer of polymer material. Where the second layer of material itself consists of multiple material layers, the plurality of electrodes may be applied to one of the multiple material layers of the second layer.

BRIEF DESCRIPTION OF THE DRAWINGS

The above and further features and advantages of the present invention will become more apparent from the following detailed description of particular embodiments of the invention with reference to the accompanying drawing figures, in which like components are designated with like reference characters, and in which.

DETAILED DESCRIPTION OF THE PREFERRED EMBODIMENTS

Figure 1:
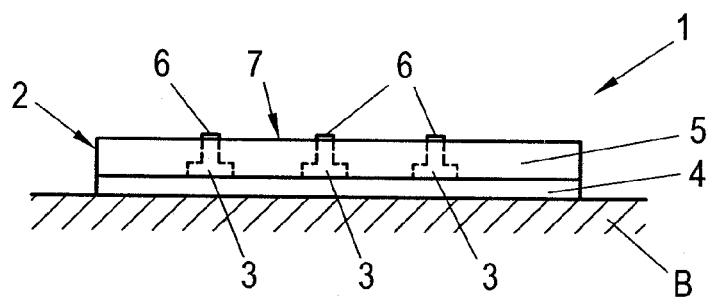
FIG. 1 is a schematic side view of a layered substrate of an electrode array according to a simple embodiment of the invention during production.

With reference firstly to FIG. 1 of the drawings, the production of an electrode array 1 according to an embodiment of the present invention is illustrated. The electrode array 1 comprises a substrate 2 for supporting a plurality of electrodes 3 and includes two layers of polymer material, namely a first layer 4, which is applied to a base or support structure B, and a second layer 5, which is applied directly to the first layer 4.

The first layer 4 of polymer material has a first coefficient of thermal expansion (CTE) and the second layer 5 of polymer material has a second coefficient of thermal expansion (CTE) which is different from the first CTE. In this instance, the first CTE (i.e. the CTE of the first layer 4) is higher than the second CTE (i.e. the CTE of the second layer 5).

After the first layer of polymer material 4 is applied on the base or support structure B, a plurality of electrodes 3, together with conductor tracks, circuitry or wiring (not shown) for connecting the electrodes 3 to an electrical source and/or to a controller, are positioned on the first layer 4. The electrodes 3 are desirably arranged spaced apart from one another to produce an array having a specific configuration. The second layer of polymer material 5 is then applied to the first layer 4 such that the plurality of electrodes 3 are substantially incorporated in the second layer 5, and such that a contact end 6 of each of the plurality of electrodes 3 extends to and/or projects from an outer surface of the substrate 2, and in particular from an outer surface 7 of the second layer 5. In this way, the electrodes 3 are incorporated within the substrate 2, but are nevertheless adapted for electrical contact with the tissue to be stimulated in a human or animal body.

Each of the first layer 4 and the second layer 5 consists of a polyimide material and these two layers 4, 5 are combined by bonding, fusing and/or curing the polyimide material at an elevated temperature, e.g. in the range of 200° C. to 400° C., while the substrate 2 is supported on the base structure B in a substantially flat configuration. In this connection, particular reference is made to the description of the curing of polyimide polymer material in U.S. Pat. No. 5,166,292. After the first and second layers 4, 5 of the substrate 2 are bonded and cured, the substrate 2 is removed from the base structure B and begins to cool.

Figure 2:
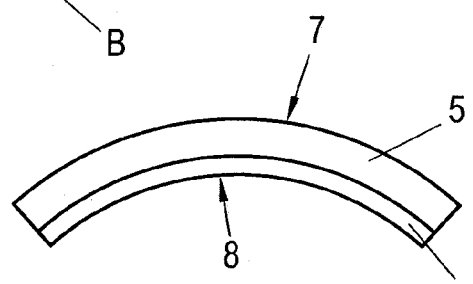
FIG. 2 is a schematic side view of a layered substrate of the electrode array shown in FIG. 1 after production.

With reference now to FIG. 2 of the drawings, as the substrate 2 cools, the temperature reduction produces differing physical responses from the first layer 4 and the second layer 5 by virtue of their differing coefficients of thermal expansion. Because the first layer 4 has a higher CTE than the second layer 5, the extent of the contraction in surface area (and in volume) experienced by the first layer 4 is significantly greater than that experienced by the second layer 5, thereby causing the substrate 2 to deform and adopt a curved profile. In particular, the first layer 4 having the higher coefficient of thermal expansion is deflected from the flat state to present a concavely curved outer surface 8, whereas the second layer 5 having the lower coefficient of thermal expansion is deformed from the flat state such that the outer surface 7 adopts a convex curvature.

Although the electrodes 3 are not specifically shown in FIG. 2, it will be appreciated that the contact ends 6 of the plurality of electrodes 3 project from the convex outer surface 7 of the substrate 2. Thus, the outer surface 7 presenting the contact ends 6 of the electrodes in the electrode array 1 of the invention is endowed with a curvature that is specifically designed to correspond with and complement the natural curvature of the bodily tissue to be stimulated.

For example, by carefully selecting the polymer material for each of the first and second layers 4, 5 of the substrate 2 (thereby setting or determining the CTE for each of these layers), and by carefully selecting and controlling the thickness of each the first and second layers 4, 5, it is thereby possible to predetermine and to generate a specific curvature in the substrate 2 for a given temperature change between the production phase and the service or operation of the device. In the present case, the electrode array of FIGS. 1 and 2 is adapted for use in a retinal implant, such that the convex curvature of the outer surface 7 is designed to match or substantially complement the concave curvature of the retina.

In this regard, and by way of specific example, the polyimide material of the first layer 4 may consist of PI-2525 which has a CTE of about 20 ppm/° C. (i.e. about $20 \times 10^{-6}$/° C.) or, alternatively, of PI-5878G which has a CTE of about 40 ppm/° C. (i.e. about $40 \times 10^{-6}$/° C.). Further polyimide materials that have a CTE within the range of about 20 to 40 ppm/° C. for use in the first layer 4 will be known to the skilled person. The polyimide material of the second layer 5, on the other hand, may consist of PI-2611 which has a CTE of about 3 ppm/° C. (i.e. $3 \times 10^{-6}$/° C.). Further polyimide materials that have a CTE within the range of 1 to 10 ppm/° C. for use in the second layer 5 will be known to the skilled person.

Figure 3:
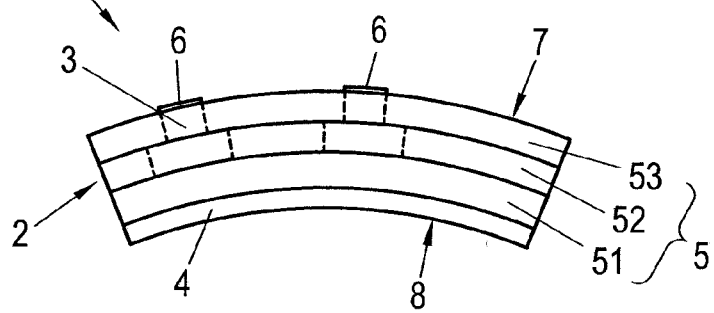
FIG. 3 is a schematic side view of an electrode array according to another preferred embodiment of the invention.

Referring now to FIG. 3 of the drawings, another preferred embodiment of the present invention is illustrated. The prime difference between this particular embodiment and the embodiment of FIG. 1 resides in the fact that the second layer of material 5 itself has a layered structure and comprises three separate material layers or "sub-layers" 51, 52, 53. Each of the individual sub-layers 51, 52, 53 is applied separately during the manufacturing method of the present invention. In particular, after the first layer 4 has been applied to the base structure B, the first sub-layer 51 of the second layer 5 is applied directly to an upper surface of the first layer 4. The electrodes 3 and their connecting conductor tracks, circuitry or wiring (not shown) are then applied on the sub-layer 51 of the second layer 5. Once the plurality of electrodes 3 are positioned on the sub-layer 51, the two further sub-layers 52, 53 are then applied to the existing first sub-layer 51.

After the second and third sub-layers 52, 53 have been applied, the plurality of electrodes 3 are substantially incorporated within the second layer 5. Nevertheless, a contact end 6 of each of the electrodes 3 extends to and/or projects from the outer surface 7 of the second layer 5 in the substrate 2 for contact with the tissue to be stimulated in the human or animal body. The substrate 2 is cured at an elevated temperature and can then be removed from the base structure B, in the same manner as described with reference to FIGS. 1 and 2 of the drawings. Thus, the embodiment in FIG. 3 is formed with a convexly curved other surface 7 to substantially complement the curvature of a retina to be stimulated with the stimulation electrode array.

The polymer material of each of the sub-layers 51, 52, 53 is most preferably the same material with the same CTE, although it may consist of different materials having different CTEs. In any case, the first layer of material 4 desirably has a higher coefficient of thermal expansion than that for all of the sub-layers 51-53 of the second layer 5. In this example, the thickness of the first layer 4 and each of the sub-layers 51, 52, 53 is about the same, namely about 5 μm. The layer thicknesses can be differently selected, however, depending on the degree of curvature required in the substrate.

Figure 4:
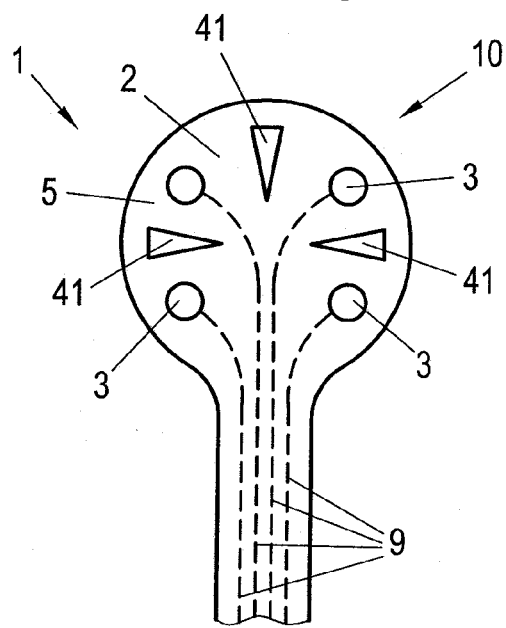
FIG. 4 is a schematic plan view of an electrode array in a medical implant device according to another preferred embodiment of the invention.
Figure 5:
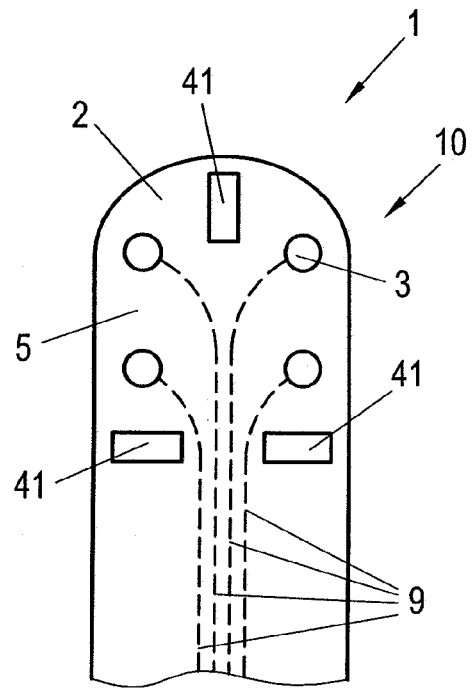
FIG. 5 is a schematic plan view of an electrode array in a medical implant device according to a further preferred embodiment of the invention.

FIG. 4 and FIG. 5 of the drawings each illustrate a portion of a medical implant device 10, particularly a retinal implant, incorporating a stimulation electrode array 1 according to the present invention. In these embodiments, the simplified, schematic illustrations of the electrode arrays 1 are shown in plan view and are shown with only four circular electrodes 3, although in practice it would, of course, be many more. Significantly, in these embodiments, rather than the first layer of material 4 being a uniform layer, the first layer 4 comprises a plurality of separate and discrete regions of material 41 having a higher coefficient of thermal expansion than the second layer of material 5. These discrete, separate regions 41 having a higher CTE may be provided in a contiguous first layer 4, or may be separate elements separated by space in the plane of the first layer 4. In the later case, the electrode 3 are typically supported by and incorporated within the second material layer 5; for example, as is the case in FIG. 3.

In FIGS. 4 and 5, the conductor tracks, circuitry or wiring 9 which connects the electrodes 3 with an electrical source and/or controller are shown in broken lines embedded within the substrate 2. The separate and discrete regions of material 41 of the first layer 4 are formed with geometric shapes—i.e. triangular in FIG. 4 and rectangular in FIG. 5—and are arranged on the substrate positioned around and between the electrodes 3. As with the embodiments in FIGS. 1 to 3, the higher CTE of the regions of material 41 of the first layer 4 compared to the CTE of the second layer 5 induces a deformation of the substrate 2 to produce a curved surface profile in the electrode array 1 for optimising stimulation of the retina tissue by the implant device 10.

It will be appreciated that the above discussion of particular embodiments of the invention with reference to the accompanying drawings is for illustrative purposes only. Accordingly, it will be appreciated that various modifications can be made in the particular parts of the embodiments described without departing from the scope of the invention as defined in the following claims.

The invention claimed is:

1. An electrode array for a medical implant device, the electrode array comprising:
   a curved substrate supporting a plurality of electrodes, the substrate comprising at least two layers of material including a first layer and a second layer,
   wherein:
      the plurality of electrodes have contact ends that extend to at least to an outer surface of the second layer of the curved substrate,
      the first layer of material and the second layer of material have different coefficients of thermal expansion, and
      the first layer and the second layer are arranged such that the coefficient of thermal expansion of the material of the first layer and the coefficient of thermal expansion of the material of the second layer cause the substrate to be curved at a normal service temperature such that the outer surface of the second layer has a convex shape.

2. An electrode array for a medical implant device, the electrode array comprising:
   a curved substrate supporting a plurality of electrodes, the curved substrate comprising at least two layers of material including a first layer and a second layer,
   wherein:
      the plurality of electrodes have contact ends that extend to at least an outer surface of the second layer of the curved substrate,
      the plurality of electrodes are incorporated in the second layer,
      the first layer of material and the second layer of material have different coefficients of thermal expansion,
      the first layer has a higher coefficient of thermal expansion than the second layer, such that the substrate is caused to be curved at a normal service temperature,
      wherein the outer surface of the second layer is on a convex side of the curved substrate.

3. An electrode array according to claim 2, wherein the first layer and the second layer of the substrate each consists of a polymer material, whereby the substrate comprises a layered polymer film.

4. An electrode array according to claim 3, wherein said polymer material is selected from the group consisting of polyimide, parlyene and silicone.

5. An electrode array according to claim 4, wherein the polymer material of the first layer is PI-2525 or PI-5878G and wherein the polymer material of the second layer is PI-2611.

6. An electrode array according to claim 2, wherein the second layer of material itself has a layered structure and comprises multiple material layers.

7. An electrode array according to claim 6, wherein the second layer incorporates the plurality of electrodes within the said multiple material layers, and wherein the electrodes extend to and/or project from an outer surface of the second layer.

8. An electrode array according to claim 2, wherein the first layer comprises a plurality of discrete or separate regions having a coefficient of thermal expansion different from the coefficient of thermal expansion of the second layer, and wherein said plurality of discrete or separate regions have a coefficient of thermal expansion in the range of about 20 ppm/° C. to about 40 ppm/° C.

9. An electrode array according to claim 8, wherein each of the discrete or separate regions in the first layer has a specific geometric shape positioned between individual electrodes of the plurality of electrodes.

10. An electrode array according to claim 2, wherein the coefficient of thermal expansion of the second layer is in the range of about 1 ppm/° C. to about 5 ppm/° C.

11. An electrode array according to claim 2, wherein the plurality of electrodes are supported on the first layer of material and wherein the outer surface of the second layer has a convex shape.

12. An electrode array according to claim 2, wherein the first layer of material is a substantially uniform layer which extends with substantially uniform thickness over the substrate.

13. An electrode array according to claim 2, wherein on the convexly curved outer surface, an end region of each of the plurality of electrodes is adapted for electrical contact with tissue in a human or animal body.

14. A medical implant device for stimulating nerve cells in a human or animal body, comprising an electrode array according to claim 2.

15. A medical implant device according to claim 14, wherein the medical implant device is a retinal implant device for stimulating nerve cells of the retina.

16. A method of manufacturing an electrode array, comprising the steps of:
applying a first layer of material having a first coefficient of thermal expansion on a base or support structure;
applying a second layer of material having a second coefficient of thermal expansion different from the first coefficient of thermal expansion on the first layer, wherein electrodes in the electrode array are incorporated into the second layer such that ends of the electrodes extend to at least an outer surface of the second layer; and
combining the first layer and the second layer to form a substrate of the electrode array at a temperature different to a normal service temperature of the electrode array,
wherein the coefficient of thermal expansion of the material of the first layer is in the range of about 20 ppm/° C. to about 40 ppm/° C. and the coefficient of thermal expansion of the material of the second layer is in the range of about 1 ppm/° C. to about 10 ppm/° C., wherein the coefficient of thermal expansion of the first layer and the coefficient of thermal expansion of the second layer cause the substrate to be curved at the normal service temperature such that an outer surface of the second layer has a convex shape.

17. A method according to claim 16, wherein the step of combining the first layer and the second layer to form the substrate of the electrode array includes bonding, fusing, and/or curing the first layer and the second layer.

18. A method according to claim 16, wherein the step of combining the first layer and the second layer takes place at an elevated temperature relative to a normal service temperature of the electrode array.

19. A method according to claim 16, wherein the step of combining the first layer and the second layer takes place on a substantially flat supporting structure, such that the substrate is substantially flat at the combining temperature.

* * * * *